United States Patent
Kukreja et al.

(10) Patent No.: US 10,247,540 B1
(45) Date of Patent: Apr. 2, 2019

(54) DETERMINING THE THICKNESS OF A SUBMICRON CARBON COATING ON A CARBON-COATED METAL BASE PLATE USING RAMAN SPECTROSCOPY

(71) Applicant: GM GLOBAL TECHNOLOGY OPERATIONS LLC, Detroit, MI (US)

(72) Inventors: Ratandeep S. Kukreja, Warren, MI (US); Misle M. Tessema, Warren, MI (US); Daad B. Haddad, Sterling Heights, MI (US)

(73) Assignee: GM GLOBAL TECHNOLOGY OPERATIONS LLC, Detroit, MI (US)

( * ) Notice: Subject to any disclaimer, the term of this patent is extended or adjusted under 35 U.S.C. 154(b) by 0 days.

(21) Appl. No.: 15/702,026

(22) Filed: Sep. 12, 2017

(51) Int. Cl.
  *G01J 3/44* (2006.01)
  *G01B 9/02* (2006.01)
  *G01N 21/65* (2006.01)
  *H01M 8/0202* (2016.01)

(52) U.S. Cl.
  CPC .......... *G01B 9/02044* (2013.01); *G01N 21/65* (2013.01); *H01M 8/0202* (2013.01)

(58) Field of Classification Search
  CPC ............ G01B 9/02044; G01B 11/0616; G01B 11/0658; G01N 21/65; G01N 2021/655; H01M 8/0202; G01J 3/44
  USPC ........................................................ 356/301
  See application file for complete search history.

(56) References Cited

U.S. PATENT DOCUMENTS

| | | | | |
|---|---|---|---|---|
| 8,298,609 B1* | 10/2012 | Liew | .................... | G11B 5/8408 427/128 |
| 2002/0122897 A1* | 9/2002 | Namiki | ................. | C23C 16/045 427/569 |
| 2011/0222180 A1* | 9/2011 | Willis | .................. | G11B 5/3106 360/31 |
| 2014/0028996 A1* | 1/2014 | Liu | ............................ | G01J 3/44 356/51 |
| 2016/0077009 A1* | 3/2016 | Gargas | ................... | G01N 21/65 356/301 |
| 2016/0289825 A1* | 10/2016 | Kim | ........................ | C23C 16/02 |

OTHER PUBLICATIONS

Raman scattering as a technique of measuring film thickness: interference effects in thin growing films, McCarty, Applied Optics, vol. 26, No. 20, Oct. 15, 1987.*

* cited by examiner

*Primary Examiner* — Tarifur R Chowdhury
*Assistant Examiner* — Jonathon Cook
(74) *Attorney, Agent, or Firm* — Reising Ethington P.C.

(57) ABSTRACT

A method of determining a thickness of a submicron carbon of a carbon-coated metal base plate that includes conducting Raman spectroscopy at a target location of the carbon-coated metal base plate to obtain a Raman shift spectrum for the target location. The Raman shift spectrum obtained at the target location is then converted into a calculated thickness of the submicron carbon coating at the target location. The conversion of the Raman shift spectrum into the calculated thickness of the submicron carbon coating at the target location may involve referencing a linear correlation that has been established over the defined wavenumber range between (1) an integrated intensity of a Raman carbon signal obtained from each of a series of reference plates that includes a submicron carbon coating having a verified thickness and (2) the verified thicknesses of the submicron carbon coatings of the series of reference plates.

18 Claims, 5 Drawing Sheets

DETERMINING THE THICKNESS OF A SUBMICRON CARBON COATING ON A CARBON-COATED METAL BASE PLATE USING RAMAN SPECTROSCOPY

INTRODUCTION

A proton-exchange membrane (PEM) fuel cell is an electrochemical device that converts the chemical energy of reactant gasses (hydrogen and an oxidant) into direct-current electricity and heat. A PEM fuel cell includes a membrane-electrode assembly (MEA) and a pair of gas-diffusion layers (GDLs). The MEA includes a proton-conductive solid polymer electrolyte, such as perfluorosulfonic acid polymer film (e.g., Nafion), that supports an anode catalyst layer on one side and a cathode catalyst layer on the other side. Generally, each of the anode and cathode catalyst layers includes a finely-divide catalyst, such as platinum, loaded onto a high-surface area catalyst support and dispersed in an ionomer. A GDL is disposed on each side of the MEA to help distribute the reactant gasses to the MEA as well as assist in other functions. In many instances, including for vehicle propulsion applications, a multitude of PEM fuel cells are arranged into a fuel cell stack to obtain increased voltage and power outputs.

Within a fuel cell stack, each pair of adjacent fuel cells is separated by a bipolar plate to facilitate the cooperative operation of the electrically interconnected PEM fuel cells. A bipolar plate has oppositely-facing major surfaces that separately define a gas flow field comprised of integrated gas flow channels that fluidly communicate with spaced apart reactant gas inlet and outlet openings that traverse the thickness of the plate. A bipolar plate serves multiple functions within the overall operation of the stack. One function of the bipolar plate is to simultaneously distribute a fuel gas (e.g. hydrogen) to the anode side of one fuel cell and an oxidant gas (e.g., oxygen) to the cathode side of the other fuel cell by way of its gas flow fields while ensuring the fuel gas and the oxidant gas are isolated from each other. Other functions of the bipolar plate include conducting electrical current between fuel cells, aiding in the removal of excess water, supporting a flow of coolant to remove heat from the fuel cells, and structurally supporting the fuel cell stack.

Bipolar plates may be comprised of a metal base plate that is covered with a conductive and corrosion-resistant protective coating to help the bipolar plate endure the various corrosive mechanisms that can occur at both of its major faces while maintaining a low interfacial contact resistance. Several metals that are commonly used to make the metal base plate include stainless steel, aluminum and its alloys, and titanium and its alloys. A thin, submicron carbon coating on top of an optional adherent interlayer may be applied to the metal base plate as the conductive and protective film. The thickness of the carbon coating has been found through durability testing to affect the extended performance of the bipolar plate. Specifically, if the carbon coating is too thin, the bipolar plate corrode prematurely and its interfacial contact resistance may rise, thus causing a decrease in electrical conductivity within the fuel cell stack and possibly resulting in premature failure of the stack.

The current ability to measure the thickness of a submicron carbon coating that covers a base metal plate, either at a single localized spot or across a larger area, is limited given the inherent constraints of standard analytical techniques. For example, ellipsometry is prone to erroneous results due to imperfections in the base metal plate and faulty calibration, and is unworkable once the gas flow fields have been stamped or otherwise formed onto the oppositely-facing surfaces of the base metal plate. Other techniques such as electron probe micro analysis (EPMA), scanning electron microscope (SEM), transmission electron microscopy (TEM), and x-ray photoelectron spectroscopy (XPS) are not only destructive in nature, but they also tend to be cost prohibitive if many samples need to be analyzed on an on-going basis and/or require an extended time period to complete the necessary preparation and analysis of single sample. The aforementioned techniques are, consequently, generally unable to accurately and non-destructively measure the thickness of the carbon coating at any one location or across a major surface of the bipolar plate both quickly and inexpensively.

The inherent limitations of standard analytical techniques for measuring submicron carbon coating thicknesses makes it difficult to implement certain practices that support fuel cell manufacturing and development operations. Indeed, a robust quality control program that can directly verify the thickness of a carbon coating to ensure it meets a minimum required thickness across the major surfaces of the bipolar plates prior to installation of the plates within a fuel cell stack is not practical using current analytical techniques since, at best, such a program would be cost prohibitive and would slow the overall manufacturing process far too much. Likewise, the ability to monitor the thickness of an applied carbon coating over time while testing the durability of a carbon-coated metallic bipolar plate is not practical, nor is it feasible to acquire carbon-coating thickness data both before and after use of the bipolar plate in a fuel cell stack to facilitate failure testing (e.g., root cause analysis) in the event that the bipolar plate suffers an unexplained performance decline during operation of the fuel cell stack. An analytical technique that can solve these issues is needed.

SUMMARY OF THE DISCLOSURE

A method of determining a thickness of a submicron carbon coating of a carbon-coated metal base plate may include several steps. In one step, a carbon-coated metal base plate may be provided that includes a metal base plate and an exteriorly-exposed submicron carbon coating over the metal base plate. In another step, Raman spectroscopy may be conducted at a target location of the carbon-coated metal base plate to obtain a Raman shift spectrum for the target location. And, in yet another step, the Raman shift spectrum obtained at the target location may be converted into a calculated thickness of the submicron carbon coating at the target location.

The aforementioned method may include other steps or be further defined. For example, the carbon-coated metal base plate may be a metallic bipolar plate that has a first major surface that defines a first gas flow field and a second major surface that defines a second gas flow field. The metal base plate may be composed of a stainless steel or some other suitable metal. Indeed, in one embodiment, the metal base plate is composed of stainless steel and a titanium interlayer is disposed between the stainless steel base plate and the exteriorly-exposed submicron carbon coating.

In one embodiment of the aforementioned method, the step of converting the Raman shift spectrum obtained at the target location into the calculated thickness of the submicron carbon coating at the target location may include several additional steps. In particular, in one step, a Raman carbon signal may be isolated from the Raman shift spectrum obtained at the target location for the carbon-coated metal base plate. In another step, the Raman carbon signal isolated from the Raman shift spectrum may be integrated over a defined wavenumber range to derive an integrated intensity of the Raman carbon signal. In still another step, a linear correlation may be established over the defined wavenumber range between (1) an integrated intensity of the Raman carbon signal obtained from each of a series of reference plates that includes a submicron carbon coating having a verified thickness and (2) the verified thicknesses of the submicron carbon coatings of the series of reference plates. And, in still another step, the linear correlation may be referenced to convert the integrated intensity of the Raman carbon signal isolated from the Raman shift spectrum into the calculated thickness of the submicron carbon coating at the target location. The defined wavenumber range may be 900 $cm^{-1}$ to 1800 $cm^{-1}$.

In another embodiment of the aforementioned method, the step of establishing the linear correlation between the integrated intensity of the Raman carbon signals obtained from the series of reference plates and the verified thicknesses of the submicron carbon coatings of the series of reference plates may include several steps. In one step, Raman spectroscopy may be conducted at a sample location on each of a series of reference plates to obtain a Raman shift spectrum associated with the sample location on each of the reference plates. Each of the series of references plates may have the same layered construction as the carbon-coated metal base plate and includes a submicron carbon coating of a verified thickness in which the verified thickness of the submicron carbon coating on each of the series of reference plates is different. In another step, a Raman carbon signal may be isolated from the Raman shift spectrum obtained at the sample location of each of the reference plates. In yet another step, the Raman carbon signal isolated from the Raman shift spectrum obtained at the sample location of each of the reference plates may be integrated over the defined wavenumber range to derive an integrated intensity of the Raman carbon signal associated with each reference plate. In still another step, a linear equation is derived in the form of y=mx that fits the integrated intensity of the Raman carbon signals associated with the reference plates when plotted against the verified thicknesses of the submicron carbon coatings of the reference plates. In this linear, "y" corresponds to the integrated intensity of the Raman carbon signal isolated from the Raman shift spectrum obtained at the sample locations over the defined wavenumber range, "x" corresponds to the verified thickness of the submicron carbon coating at the sample locations, and "m" is the slope representing the change in the integrated intensity of the Raman carbon signal over the change in the verified thickness of the submicron carbon coatings.

The aforementioned method may include still other steps. For instance, in carrying out the method, Raman spectroscopy may be conducted at a plurality of target locations spread across a surface of the carbon-coated metal base plate to obtain a Raman shift spectrum for each of the plurality of target locations. The Raman shift spectrum obtained at each of the plurality of target locations may be converted into a calculated thickness of the submicron carbon coating at each of the plurality of target locations. Still further, the calculated thickness of the submicron carbon coating at each of the plurality of target locations may be compared against a minimum required coating thickness for the submicron carbon coating to verify whether the submicron carbon coating meets or exceeds the minimum required coating thickness across the surface of the carbon-coated metal base plate Another method of determining a thickness of a submicron carbon of a carbon-coated metal base plate may include several steps. In one step, a beam of monochromatic light may be directed at each of a plurality of target locations spread across a surface of a carbon-coated metal base plate. In another step, inelastic scattered light reemitted from each of the plurality of target locations may be detected to obtain a Raman shift spectrum for each of the plurality of target locations. In yet another step, a Raman carbon signal may be isolated from the Raman shift spectrum obtained at each of the plurality of target locations. In still another step, the Raman carbon signal isolated from the Raman shift spectrum obtained at each of the plurality of target locations may be integrated over a defined wavenumber range to derive an integrated intensity of the Raman carbon signal. Still further, in another step, a linear correlation may be established over the defined wavenumber range between (1) an integrated intensity of a Raman carbon signal obtained from each of a series of reference plates that includes a submicron carbon coating having a verified thickness and (2) the verified thicknesses of the submicron carbon coatings of the series of reference plates. In another step, the linear correlation may be referenced to convert the Raman carbon signal isolated from the Raman shift spectrum obtained at each of the plurality of target locations into a calculated thickness of the submicron carbon coating at each of the plurality of target locations.

The aforementioned method may include other steps or be further defined. For example, the calculated thickness of the submicron carbon coating at each of the plurality of target locations may be compared against a minimum required coating thickness of the submicron carbon coating to verify whether the submicron carbon coating meets or exceeds the minimum required coating thickness across the surface of the carbon-coated metal base plate. As another example, the linear correlation may be a linear equation in the form of y=mx in which "y" corresponds to the integrated intensity of the Raman carbon signal isolated from the Raman shift spectrum obtained at the sample locations over the defined wavenumber range, "x" corresponds to the verified thickness of the submicron carbon coating at the sample locations, and "m" is the slope representing the change in the integrated intensity of the Raman carbon signal over the change in the verified thickness of submicron carbon coatings.

Additionally, the carbon-coated metal base plate may be a metallic bipolar plate that has a first major surface that defines a first gas flow field and a second major surface that defines a second gas flow field. The metal base plate may be composed of a stainless steel or some other suitable metal. Indeed, in one embodiment, the metal base plate may be composed of stainless steel and a titanium interlayer may be disposed between the stainless steel base plate and the exteriorly-exposed submicron carbon coating. Still further, the defined wavenumber range may be 900 $cm^{-1}$ to 1800 $cm^{-1}$, and, separately, the plurality of target locations may include anywhere from two to forty target locations.

Another method of determining a thickness of a submicron carbon of a metallic bipolar plate may include several steps. In one step, a metallic bipolar plate may be provided that includes a metal base plate and an exteriorly-exposed submicron carbon coating overlying the metal base plate. The bipolar plate has a first major surface that defines a first gas flow field and an oppositely-facing second major surface that defines a second gas flow field. In another step, a calculated thickness of the submicron carbon coating at a plurality of target locations spread across at least one of the first major face or the second major face of the bipolar plate may be determined. To determine the calculated thickness of the submicron carbon coating at each target location, Raman spectroscopy may be conducted at the target location to obtain a Raman shift spectrum for the target location and, thereafter, the Raman shift spectrum may be converted into the calculated thickness of the submicron carbon coating at the target location. In yet another step, the calculated thickness of the submicron carbon coating at each of the plurality of target locations may be compared against a minimum required coating thickness for the submicron carbon coating to verify whether the submicron carbon coating meets or exceeds the minimum required coating thickness across at least one of the first major face or the second major face of the bipolar plate.

The aforementioned method may include other steps or be further defined. For example, the step of converting the Raman shift spectrum into the calculated thickness of the submicron carbon coating at each of the plurality of target locations may include several steps. In one step, a Raman carbon signal may be isolated from the Raman shift spectrum obtained at the target location. In another step, the Raman carbon signal isolated from the Raman shift spectrum may be integrated over a defined wavenumber range to derive an integrated intensity of the Raman carbon signal. In yet another step, a linear correlation may be established over the defined wavenumber range between (1) an integrated intensity of a Raman carbon signal obtained from each of a series of reference plates that includes a submicron carbon coating having a verified thickness and (2) the verified thicknesses of the submicron carbon coatings of the series of reference plates. And, in still another step, the linear correlation may be referenced to determine the calculated thickness of the submicron carbon coating at the target location. The defined wavenumber range may be 900 cm$^{-1}$ to 1800 cm$^{-1}$ when carrying out the conversion of the Raman shift spectrum into the calculated thickness of the submicron carbon coating at each of the plurality of target locations.

DETAILED DESCRIPTION

A method of determining the thickness of a submicron carbon coating of a carbon-coated metal base plate that entails the use of Raman spectroscopy is disclosed. The disclosed method involves first providing a carbon-coated metal base plate that includes an exteriorly exposed submicron carbon coating of less than 1 μm. The carbon-coated metal base plate may be a metallic bipolar plate for PEM fuel cell stack applications or some other similarly-coated substrate. Next, Raman spectroscopy is conducted at one or more target locations on a surface of the carbon-coated metal base plate to obtain a Raman shift spectrum associated with each of the one or more target locations. The Raman shift spectrum associated with each of the one or more target locations is then converted into a calculated thickness of the submicron carbon coating at the one or more target locations. Other additional steps may further be practiced as part of the disclosed method including, for example, comparing the calculated thickness of the submicron carbon coating at each of the one or more target locations against a minimum required thickness to verify that the submicron coating meets or exceeds the minimum required thickness across the analyzed surface of the carbon-coated metal base plate.

The conversion of the Raman shift spectrum obtained at each target location into a calculated thickness of the submicron carbon coating is made possible because of a discovery that a relationship can be established between the Raman shift spectrum and the thickness of the submicron carbon coating. That relationship may be a linear correlation between an integrated intensity of the portion of the Raman shift spectrum attributable to a submicron carbon coating (i.e., the Raman carbon signal) and a verified thickness of the submicron carbon coating over the defined wavenumber range. To that end, each of a series of reference plates that has submicron carbon coating of a certain verified thickness can be subjected to Raman spectroscopy at a sample location to establish a linear correlation between the integrated intensity of the Raman carbon signals obtained from the reference plates and the verified thicknesses of the submicron carbon coatings of the reference plates. Once that linear correlation is established using the series of reference plates, the integrated intensity of the Raman carbon signal at each of the one or more target locations of the carbon-coated metal base plate can reference the linear correlation to determine the calculated thickness of the submicron carbon coating at the target location(s).

The disclosed method can accurately determine the thickness of an applied submicron carbon coating at the target location(s) of the carbon-coated metal base plate without requiring the destruction of the plate being analyzed. This capability allows the thickness of an applied submicron carbon coating to be determined at multiple target locations spread across a surface of the carbon-coated metal base plate to essentially "map" the thickness of the carbon coating over an extended area. Taking into account the establishment of the linear correlation to be used in association with the target locations, any intermittent calibration of the linear correlation, and the analysis of the carbon-coated metal base plate, the disclosed method can be performed relatively quickly and inexpensively over time compared to other standard analytical techniques. The disclosed method may therefore be used to verify that the thickness of a submicron carbon coating meets or exceeds a minimum required thickness as part of a quality control program. The disclosed method may also support other applications including durability testing and failure analysis.

Figure 1:
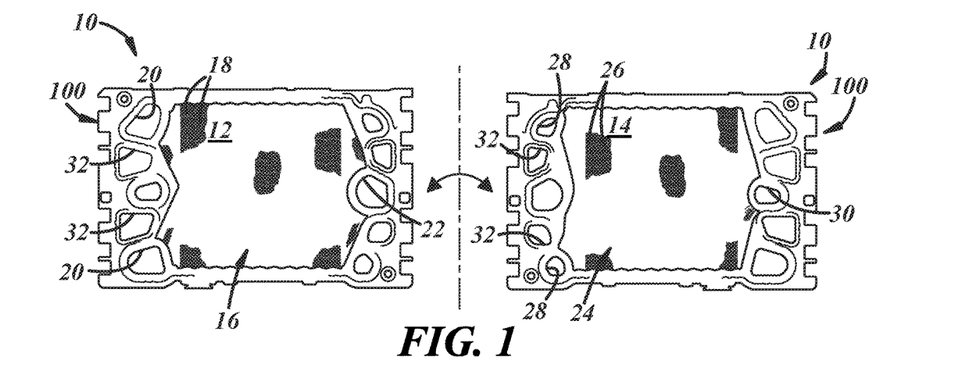
FIG. 1 is a representative perspective view of both sides of a carbon-coated metal base plate in the form of a metallic bipolar plate according to one embodiment of the present disclosure that includes a submicron carbon coating having a thickness that can be measured at one or more target locations using Raman spectroscopy.
Figure 2:
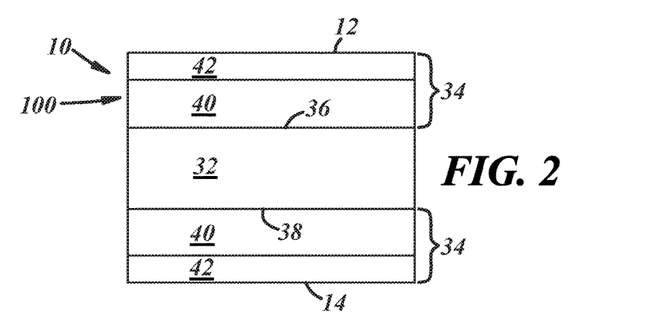
FIG. 2 is a magnified and idealized cross-sectional view of the metallic bipolar plate shown in FIG. 1 depicting a metal base plate and a conductive and corrosion-resistant protective coating, which includes a submicron carbon coating, that overlies the metal base plate according to practices of the present disclosure.

Referring now to FIGS. 1-10, one particular example of the disclosed method is demonstrated. The practice of the disclosed method is applicable to a carbon-coated metal base plate 10, which, as shown here in FIGS. 1-2, is depicted in the form of a metallic bipolar plate 100 that includes a first major face 12 and an oppositely-facing second major face 14. The first major face 12 defines a first gas flow field 16 comprised of integrated gas flow channels 18 that meander along the first major face 12 and fluidly communicate with a hydrogen inlet opening 20 and a hydrogen outlet opening 22. Likewise, the second major face 14 defines a second gas flow field 24 comprised of integrated gas flow channels 26 that meander along the second major face 14 and fluidly communicate with an oxidant gas inlet opening 28 and an oxidant gas outlet opening 30. Each of the hydrogen inlet opening 20, the hydrogen outlet opening 22, the oxidant gas inlet opening 28, and the oxidant gas outlet opening 30 traverses a thickness of the bipolar plate 10. Other openings such as coolant openings 32 and fastener openings 34 may also traverse a thickness of the bipolar plate 10 outside of the gas flow fields 16, 24.

The first and second gas flow fields 16, 24 are fluidly isolated from each other so that hydrogen supplied to the first gas flow field 16 and an oxidant gas supplied to the second gas flow field 24 cannot intermix when those gasses are supplied to their respective flow fields 16, 24 during use of the bipolar plate 100. Indeed, when the metallic bipolar plate 100 is positioned between two adjacent PEM fuel cells within a fuel cell stack, hydrogen is passed through the first gas flow field 16 from the hydrogen inlet opening 20 to the hydrogen gas outlet opening 22, and an oxidant gas such as air or oxygen is passed through the second gas flow field 24 from the oxidant gas inlet opening 28 to the oxidant gas outlet opening 30. The first gas flow field 16 distributes hydrogen through a GDL to an anode catalyst layer of one MEA and the second gas flow field 24 distributes the oxidant gas through a GDL to a cathode catalyst layer of another MEA. In that sense, the first major face 12 of the bipolar plate 100 may be referred to as the "anode side" of the plate 100 while the second major face 14 may be referred to as the "cathode side" of the plate 100.

Referring now specifically to FIG. 2, the bipolar plate 100 may be constructed from a base metal plate 32 that includes a conductive and corrosion-resistant protective coating 34 that overlies the base metal plate 32. The base metal plate 32 may be composed of a metal that has good electrical and thermal conductivities, is chemically stable and corrosion resistant, has a low permeability for hydrogen, has a low thermal expansion, has good mechanical stability, and is easily formable, among other characteristics. Several metals that may serve as the base metal plate 32 include stainless steel, aluminum and its alloys, and titanium and its alloys. Austenitic stainless steels such as 304 and 316 stainless steels are commonly used. The base metal plate 32 includes a first metal surface 36 and a second metal surface 38 that are separated by a thickness of the base metal plate 32, which may range from 50 µm to 100 µm. The first metal surface 36 and the second metal surface 38 correspond to and delineate the overall shape of the first major face 12 and the second metal face 14 of the bipolar plate 100, respectively.

The conductive and protective coating 34 may include a titanium interlayer 40 and a submicron carbon coating 42, as shown. The titanium interlayer layer 40 is applied over the first and second metal surfaces 36, 38 of the metal base plate 32 to a thickness ranging from 40 µm to 80 µm and the submicron carbon coating 42 is applied over the titanium interlayer 40. Each of the titanium interlayer 40 and the submicron carbon coating 42 may be deposited by any of a wide variety of know thin-film coating techniques. During manufacture of the bipolar plate 100, the conductive and protective coating 34 may first be applied to the base metal plate 32 to form a coated precursor plate. Then, subsequent to the deposition of the conductive and protective coating 34, the coated precursor plate may be stamped to form the first and second gas flow fields 16, 24 and to complete the fabrication of the bipolar plate 10. As such, the term "carbon-coated metal base plate" as used herein encompasses the fabricated bipolar plate 100 shown in FIG. 1 as well as the coated precursor plate (not shown) that exists prior to formation of the first and second gas flow fields 16, 24. The disclosed method may be performed on each type of carbon-coated metal base plate.

The submicron carbon coating 42 includes amorphous carbon and has a thickness in the submicron range of less than 1 µm. At least 90 wt % of the submicron carbon coating 42 may be amorphous carbon with very little, e.g., 10 wt % or less, being crystalline prior to use of the bipolar plate 100 in a fuel cell stack. Preferably, at least 98 wt %, or more preferably at least 99 wt %, of the submicron carbon coating 42 is amorphous carbon. The submicron carbon coating 42 is the outermost material of the bipolar plate 100 and, accordingly, is directly exposed to the hydrogen and oxidant gases that flow through the first and second gas flow fields 16, 24 of the bipolar plate 100 when in use. The main purpose of the submicron carbon coating 42 is to improve the electrical conductivity of the bipolar plate 100 while also enhancing its chemical and corrosion resistance. Through durability testing of carbon-coated metallic bipolar plates, including ones similar to that shown in FIGS. 1-2, it was found that the fuel cell modules being tested had a tendency to fail as a result of an increase in high-frequency resistance of the bipolar plates when the submicron carbon coatings were too thin. A minimum required thickness of the submicron carbon coating 42, which can be as low as 10 nm, may therefore be needed to help maintain a low interfacial contact resistance to support long term stability of an operating fuel cell stack.

Figure 3:
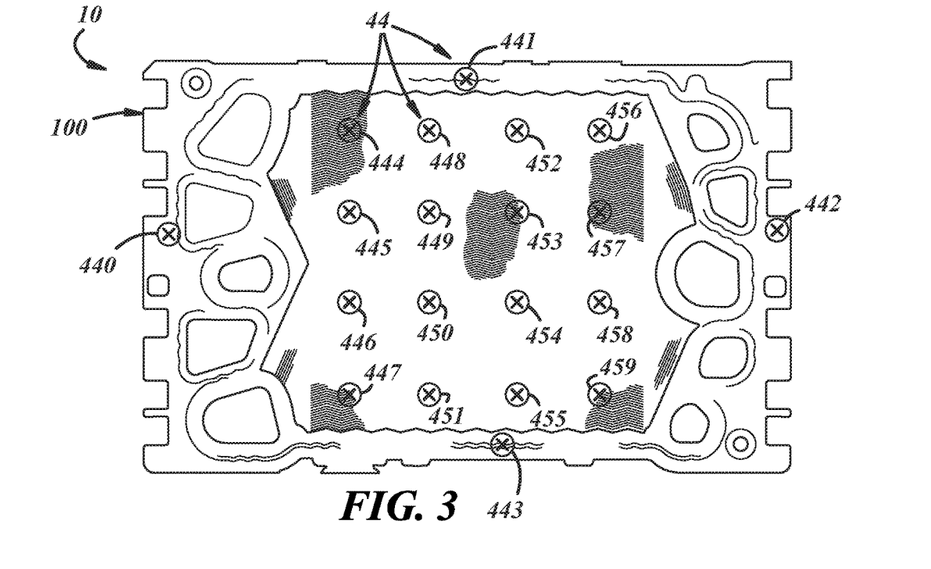
FIG. 3 is a plan view of a carbon-coated metal base plate in the form of a metallic bipolar plate with a plurality of target locations identified where the thickness of the submicron carbon coating is to be determined according to practices of the present disclosure.

Referring now to FIG. 3, an application of the disclosed method is shown and described in which Raman spectroscopy is used to determine the thickness of the submicron carbon coating 42 at a plurality of target locations 44 spread across the first major face 12 of the bipolar plate 100 so that, in applicable contexts, the reported thickness and uniformity of the coating 42 can be verified or changes in the thickness of the coating 42 can be monitored. Here, the disclosed method is demonstrated in connection with only the first major face 12 of the bipolar plate 100 shown in FIGS. 1-2. It should be appreciated, however, that the same method can be performed on the second major face 14 in the same way for the same reasons. The disclosed method may also be performed in conjunction with other carbon-coated metal base plates besides the bipolar plate 100 including, for example, a coated precursor plate that has yet to undergo stamping or some other operation to form the first and second gas flow fields 16, 24 of the first and second major faces 12, 14 of the bipolar plate 100, respectively.

The number of target locations 44 spread across the first major face 12 where the thickness of the submicron carbon coating 42 is measured may vary depending on how many data points are needed for a given application. In typical scenarios, the number of target locations may vary two to one hundred, or more narrowly from five to forty. Many of the target locations 44—e.g., at least 50% or even at least 80%—may be contained within the first gas flow field 16 since that area of the first major face 12 of the bipolar plate 100 is the portion that is directly exposed to hydrogen gas on a continuous basis. In the embodiment shown here in FIG. 3, for example, the plurality of target locations includes twenty target locations, which are individually identified by reference numerals 440-459, and sixteen of those target locations 444-459 are contained within the first gas flow field 16. Of course, the number of target locations 44 does not necessarily have to include a plurality of target locations 44. In certain embodiments, the thickness of the submicron carbon coating 42 may be determined at only one target location 44 if that a particular spot needs to be analyzed for some reason but not any others.

The thickness of the submicron carbon coating 42 is determined or measured at each of the one or more target locations 44 using Raman spectroscopy. But first, in order to determine the thickness of the submicron carbon coating 42 on the bipolar plate 100, a relationship between the Raman shift spectrum that is generated by Raman spectroscopy and the thickness of the submicron carbon coating 42 is established for the target location(s) 44. This relationship is needed since Raman spectroscopy does not directly measure the thickness of an applied thin-film coating; rather, it is a form of spectroscopy that observes vibrational, rotational, and other low-frequency modes in a sample of a Raman active material, which have long been used to provide detailed information about chemical structure, phase and polymorphy, crystallinity, and molecular interactions. The pertinent relationship employed here is based on the finding that, in general, the integrated intensity of a Raman carbon signal has a linear correlation to the thickness of a submicron carbon coating over a defined wavenumber range, as will be explained in greater detail below.

Figure 4:
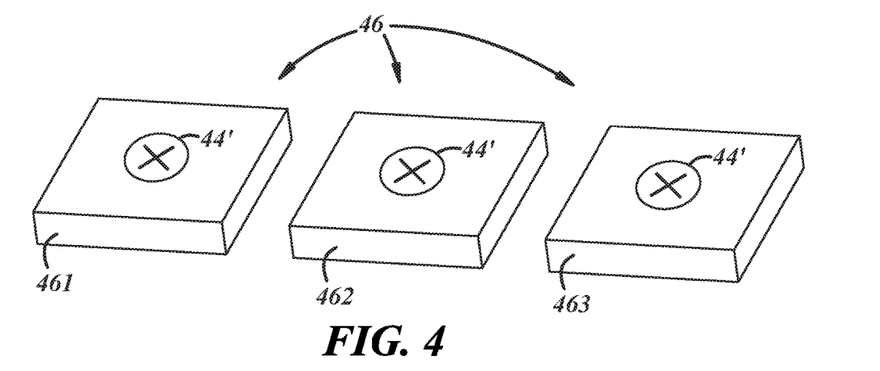
FIG. 4 is a perspective view of a series of reference plates with a sample location identified on the reference plates according to practices of the present disclosure.

To derive the requisite relationship between the Raman shift spectrum and the thickness of the submicron carbon coating 42, each of a series of reference plates 46 is first subjected to Raman spectroscopy at a sample location 44', as illustrated in FIG. 4. The sample location 44' depicted on each of the reference plates in FIG. 4 is identified individually by reference numerals 441'-443'. In order to obtain an accurate relationship, each of the series of reference plates 46 has the same layered structure as the carbon-coated metal base plate 10 sought to be analyzed including a metal base plate 32' having the same composition as the metal base plate 32 of the carbon-coated metal base plate 10 and an overlying conductive and protective coating 34' having the same number of layers with the same compositions as the conductive and protective coating 34 of the carbon-coated metal base plate 10. In other words, if bipolar plates 100 having stainless steel base plates that are covered with a titanium interlayer that supports a submicron carbon coating are intended to be analyzed, then the metal base plate 32' of each of the references plates 46 is also composed of stainless steel and the conductive and protective coating 34' that overlies the stainless steel base plate 32' also includes a titanium interlayer that supports a submicron carbon coating.

Figure 5:
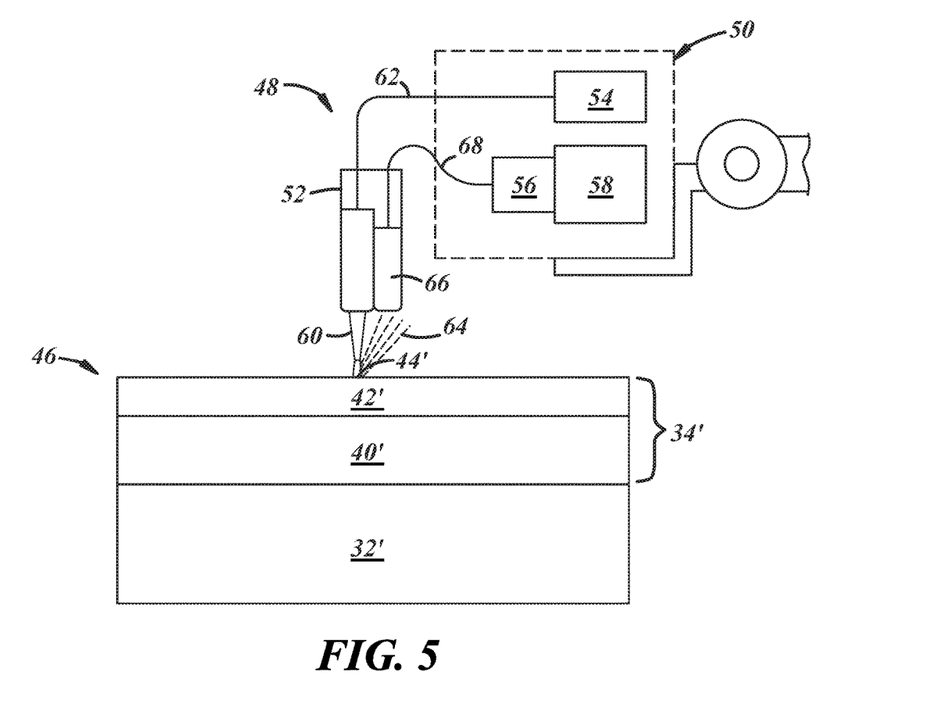
FIG. 5 is a generic and idealized cross-sectional view of one of the reference plates shown in FIG. 4 along with a schematic illustration of a Raman spectrometer according to practices of the present disclosure.

Each of the series of reference plates 46 that is analyzed by Raman spectroscopy has a submicron carbon coating 42' of a known and verified thickness. The submicron carbon coating 42' of one of the reference plates 46 is illustrated in FIG. 5 and, like the carbon-coated metal plate 10, overlies a titanium interlayer 40' which in turn overlies the metal base plate 32'. The submicron carbon coating 42' on each of the reference plates 46 has a different verified thickness so that sufficient data points are available to confidently derive the requisite relationship between the Raman shift spectrum and the thickness of the submicron carbon coating 42. For example, the number of reference plates 46 that are subjected to Raman spectroscopy may be between two and ten or, more narrowly, between three and five, and the thickness of the submicron carbon coating 42' of each of the plates 46 may range somewhere between 2 nm and 50 nm. In the embodiment shown in FIG. 4 and for illustrative purposes to help better explain the disclosed method, the series of reference plates 46 depicted includes three reference plates 461, 462, 463 that have verified submicron carbon coating thicknesses of 6 nm, 12 nm, and 17 nm, respectively. The carbon coating thicknesses may be verified by performing SEM, TEM, or some other suitable technique in the immediate vicinity of the sample locations 44'.

Raman spectroscopy is carried out at each of the sample locations 44' of the reference plates 46 with a Raman spectrometer 48. For ease of movement and manipulation relative to the reference plates 46 and the carbon-coated metal base plate(s) 10, the Raman spectrometer is preferably a portable Raman spectrometer 50, such as the I-Raman Plus portable spectrometer available from B&W Tek (bwtek.com), that is mounted on a robotically-movable arm. As shown schematically in FIG. 5, the portable Raman spectrometer 50 may include a probe 52, an excitation source 54, a wavelength selector 56, and a detector 58. At each sample location 44' of the reference plates 46, the probe 52 delivers a beam of monochromatic light 60—typically a laser beam—at a wavelength in the ultraviolet (UV), visible, or near-infrared (NIR) range to the reference plate 46. For purposes of working with amorphous carbon, the beam of monochromatic light 60 preferably has a wavelength of 532 nm. The beam of monochromatic light 60 is generated by the excitation source 54 and supplied to the probe 52 through a fiber optic cable 62. The beam of monochromatic light 60 delivered by to the probe 52 impinges the reference plate 46 at the sample location 44'. The incident beam of monochromatic light 60 interacts with the materials of the reference plate 46 at the sample location 44' and some of the light is reemitted as scattered light 64.

The scattered light 64 is either elastic or inelastic. The vast majority of the scattered light 64 is elastic or Rayleigh scattering that has the same frequency and thus the same wavelength of the incident beam of monochromatic light 60. A very small amount, e.g., approximately 0.001%, of the scattered light 64 is inelastic scattering that has a lower frequency (lower energy Stokes scattering) or a higher frequency (higher energy anti-Stokes scattering) than the incident beam of monochromatic light 60 and, thus, manifests itself as a shift in wavelength from the monochromatic light 60 known as a Raman shift. The scattered light 64 emitted from the sample location 44' is collected and filtered by a collector 66, which includes optical and filtering components, to remove elastic scattered light. The inelastic scattered light is then delivered to the wavelength selector 56 through a fiber optic cable or a bundle of fiber optic cables 68. The wavelength selector 56 may be a spectrophotometer having a transmission grating, an interference filter, or some other device that can separate the inelastic scattered light by wavelength. The separated inelastic scattered light is delivered from the wavelength selector 56 to the detector 58 where the intensity of the Raman shift is recorded at each wavelength.

Figure 6:
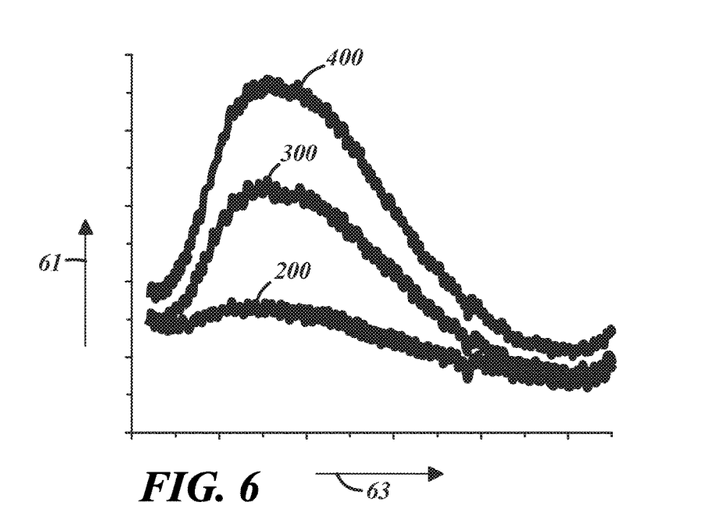
FIG. 6 illustrates a Raman spectrum generated at the sample location of each of the reference plates shown in FIG. 4 on the same chart for ease of comparison, wherein the y-axis is the intensity of the Raman shift in cps and the x-axis is the Raman shift in wavenumber (cm$^{-1}$)

The data recorded by the detector 58 is presented as a Raman shift spectrum which plots intensity of the observed Raman shift (in counts or counts per second (cps)) versus wavelength (often expressed as wavenumbers in $cm^{-1}$) of the Raman shift. Usually, only inelastic Stokes scattering is used to develop a Raman shift spectrum because it is more intense than inelastic anti-Stokes scattering. Referring now to FIG. 6, the Raman spectrum generated at the sample locations 44' of the reference plates 461, 462, 463 is shown representatively on the same chart for ease of comparison. The Raman shift spectrum for the reference plate 461 having a submicron carbon coating thicknesses of 6 nm is identified by reference numeral 200; the Raman shift spectrum for the reference plate 462 having a submicron carbon coating thicknesses of 12 nm is identified by reference numeral 300; and the Raman shift spectrum for the reference plate 463 having a submicron carbon coating thicknesses of 17 nm is identified by reference numeral 400. Here, in FIG. 6, the intensity of the Raman shift in cps increases on the y-axis in the direction of arrow 61 and the Raman shift in wavenumber increases on the x-axis in the direction of arrow 63. As can be seen, the intensity profile of the Raman shift is proportional to the thickness of the submicron carbon coating 42' at the sample location 44' of the reference plates 46 over a particular wavenumber range.

As previously mentioned, a linear correlation exists between integrated intensity of the Raman carbon signals of the Raman shift spectrums obtained from the sample locations 44' and the verified thicknesses of the submicron carbon coating 42' (which can be used to calculate the thickness of the submicron carbon coating 42 of the carbon-coated metal base plate 10) over a defined wavenumber range. A Raman carbon signal is essentially the isolated contribution of the submicron carbon coating 42' to the Raman shift spectrum; in other words, it is portion of the Raman shift spectrum that is attributable to the submicron carbon coating 42'. The Raman shift spectrum derived from the sample locations 44' may be filtered to isolate a Raman carbon signal associated with the sample location 44' of each reference plate 46. To obtain the Raman carbon signal from the Raman shift spectrum at each of the sample location 44', the effects of the other components of the reference plate 46—here, the titanium interlayer 40' and the metal base plate 32'— are removed from the spectrum. This can be accomplished by approximating the portion of the Raman shift spectrum that is not attributable to the submicron carbon coating 42' at each sample location 44' and then subtracting that data from its associated spectrum, especially since a way to closely approximate the portion of the Raman shift spectrum that is not attributable to the submicron carbon coating 42' has been discerned.

Figure 7:
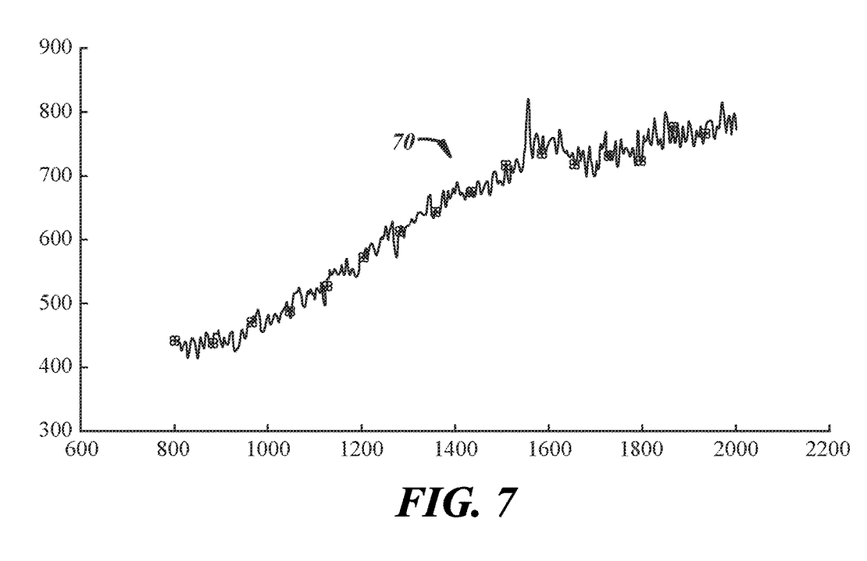
FIG. 7 is a Raman shift spectrum generated at the sample location of one of the reference plates using Raman spectroscopy according to practices of the present disclosure, wherein the y-axis is the intensity of the Raman shift in counts and the x-axis is the Raman shift in wavenumber (cm$^{-1}$)

At each reference plate 46, the Raman carbon signal can be isolated by subtracting the approximated contribution of the other components of the reference plate 46 at the sample location 44' from the Raman shift spectrum, as shown in FIGS. 7-10. First, as shown in FIG. 7, a Raman shift spectrum 70 of the reference plate 46 at the sample location 44' is generated by conducting Raman spectroscopy as described above. The defined wavenumber range (x-axis) that provides useful data for amorphous carbon has been determined to be 900 $cm^{-1}$ to 1800 $cm^{-1}$. In that regard, the intensities of the Raman shift (y-axis) may be recorded over a larger range that extends beyond the defined wavenumber range in order to capture the relevant data. To be sure, in many instances, the Raman shift spectrum of the sample location 44' may be plotted over a wavenumber range of 800 $cm^{-1}$ to 2000 $cm^{-1}$, although other ranges are certainly possible as part of the disclosed method. In FIG. 7, the units of the Raman shift on the x-axis are wavenumber ($cm^{-1}$) and the units of the intensity on the y-axis are counts.

Figure 8:
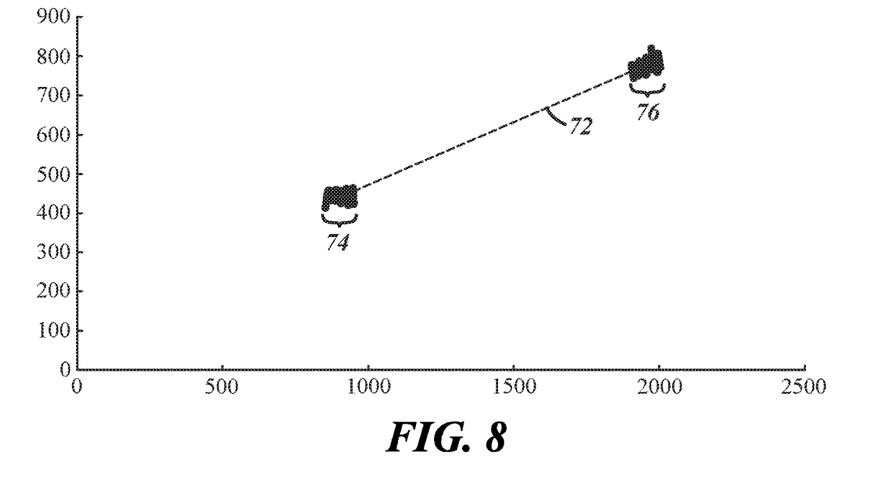
FIG. 8 illustrates a background baseline that represents the contribution to the Raman shift spectrum of the other components of the reference plate over the defined wavenumber range and, consequently, may be subtracted from the Raman shift spectrum to derive and isolate a Raman carbon signal from the Raman shift spectrum according to practices of the present disclosure, wherein the y-axis is the intensity of the Raman shift in counts and the x-axis is the Raman shift in wavenumber (cm$^{-1}$)

Next, as shown in FIG. 8, a background baseline 72 that represents the contribution to the Raman shift spectrum 70 of the other components of the reference plate 46 is established over the defined wavenumber range. For example, the intensities of the Raman shift spectrum 70 between 850 $cm^{-1}$ and 950 $cm^{-1}$ and the intensities between 1900 $cm^{-1}$ and 2000 $cm^{-1}$ are selected to the exclusion of the intervening portion of the Raman shift spectrum to define first and second background wavenumber intervals 74, 76 proximate to the ends of the defined wavenumber range. The background baseline 72 may then be established as a linear equation that extends between and fits the intensity data within the first and second background wavenumber intervals 74, 76 using regression analysis such as the ordinary least squares method. The ordinary least squares method fits a straight regression line through the data points such that the sum of the squared residuals (i.e., the sum of the vertical distances between the data points and the regression line) is minimized.

Figure 9:
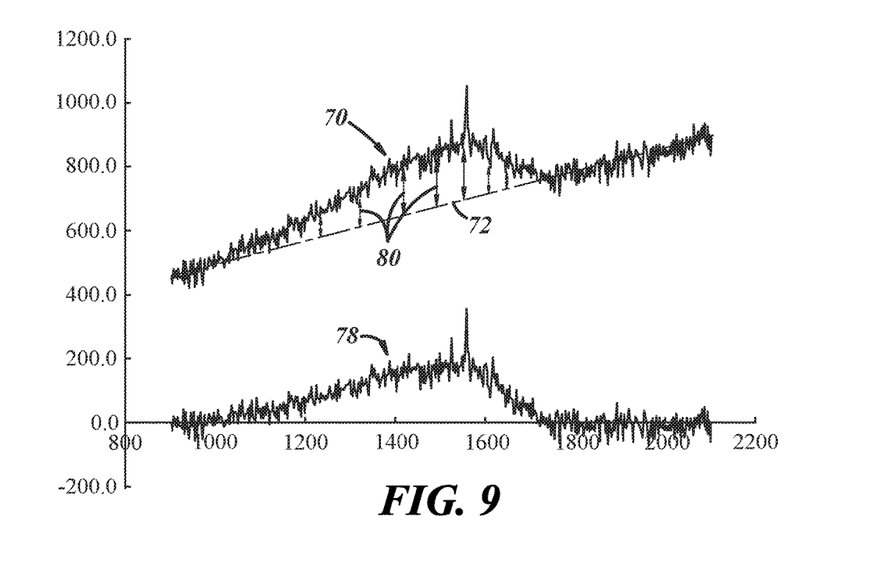
FIG. 9 illustrates how the Raman carbon signal is derived by subtracting the background baseline shown in FIG. 8 from the Raman shift spectrum according to practices of the present disclosure, wherein the y-axis is the intensity of the Raman shift in counts and the x-axis is the Raman shift in wavenumber (cm$^{-1}$)

Once established, the background baseline 72 is subtracted from the Raman shift spectrum 70 to derive a Raman carbon signal 78, as shown in FIG. 9. The Raman carbon signal 78 (lower plot), as shown, is the difference between the intensities of the Raman shift spectrum 70 and the intensities represented by the background baseline 72 along the defined wavenumber range of 900 $cm^{-1}$ to 1800 $cm^{-1}$, as illustrated by arrows 80 in the upper plot. The Raman carbon signal 78 is then integrated between the defined wavenumber range of 900 $cm^{-1}$ to 1800 $cm'$ to compute the integrated intensity of the Raman carbon signal over the defined wavenumber range at the sample location 44'. This same procedure is performed at the sample locations 44' of the other reference plates 46 and the integrated intensities of the Raman carbon signals are plotted as integrated intensity data points 82 as shown in FIG. 10; that is, the integrated intensity of the Raman carbon signal 78 of each sample location 44' of the reference plates 46 is compiled and plotted together to show how the integrated intensity of the Raman carbon signal changes as a function of the verified thickness of the submicron carbon coatings 42' on the reference plates 46.

Figure 10:
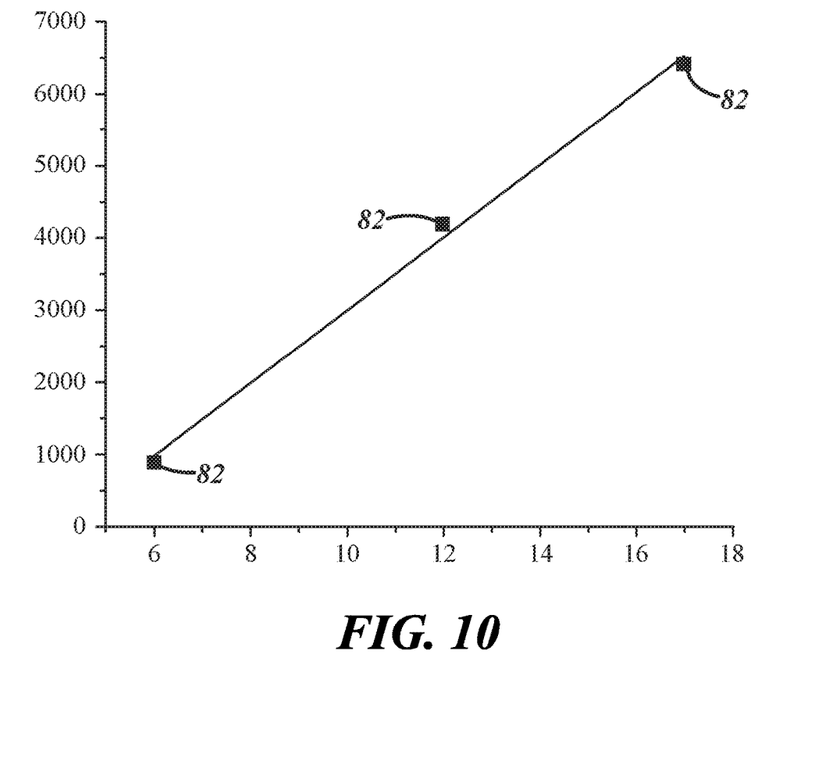
FIG. 10 is a plot of the integrated intensity of the Raman carbon signal obtained from the sample locations on the series of reference plates against the verified thicknesses of the submicron carbon coatings of the reference plates according to practices of the present disclosure, which can be used to determine a calculated thickness of the submicron carbon coating at the one or more target locations on the carbon-coated metal base plate being analyzed, wherein the y-axis is the integrated intensity of the Raman carbon signal over the defined wavenumber range and the x-axis is the verified thickness of the submicron carbon coating in nanometers (nm).

FIG. 10 represents, more specifically, one exemplary implementation in which the integrated intensity of the Raman carbon signal 78 for a common sample location 44' of the three reference plates 461, 462, 463 illustrated in FIG. 4 is plotted. Indeed, the integrated intensity of the Raman carbon signal obtained from one sample location 44' on the reference plate 461 having a verified submicron carbon coating thickness of 6 nm is shown in the lower left-hand corner of the graph. Similarly, the integrated intensity of the Raman carbon signal obtained from the same sample location 44' of the reference plate 462 having a verified submicron carbon coating thickness of 12 nm is shown in the middle of the graph. And, still further, the integrated intensity of the Raman carbon signal obtained from the same sample location 44' of the reference plate 463 having a verified submicron carbon coating thickness of 17 nm is shown in the upper right-hand corner of the graph. This very same graph is produced for each of the sample locations 44' across the reference plates 46 and, accordingly, may include a different number of data points depending on the number of reference plates 46 analyzed.

A linear correlation between the integrated intensity of the Raman carbon signals 78 (i.e., the integrated intensity data points 82) and the verified thicknesses of the submicron carbon coating 42' across the reference plates 46 can now be established. The linear correlation may be in the form of an equation that fits the integrated intensity data points 82 obtained from the reference plates 46 and plotted against the verified thicknesses of the submicron carbon coating 42'. The equation may be in the form of $y=mx$, in which "y" corresponds to the the integrated intensity in counts of the Raman carbon signal 78 over the defined wavenumber range, "x" corresponds to the verified thickness of the submicron carbon coating 42' in nanometers (nm), and "m" is the slope representing the change in the integrated intensity of the Raman carbon signal 78 over the change in the verified thickness of the submicron carbon coating 42' ($\Delta y/\Delta x$). This equation may be fit to the integrated intensity data points 82 of the known and verified submicron carbon coating thicknesses of the reference plates 46 by any suitable regression analysis including, for example, the ordinary least squares method already described above.

The linear correlation thus established using the reference plates 46 may now be used globally as the relationship between the Raman shift spectrum and the thickness of the submicron carbon coating 42 at each target location 44 of the carbon-coated metal base plate 10, which enables the thickness of the submicron carbon coating 42 to be calculated at each of the target locations 44 with confidence in a relatively simple, quick, and inexpensive manner. Specifically, Raman spectroscopy may be conducted at each of the target locations 44 of interest in the same manner as described above in connection with FIG. 5 to obtain a Raman shift spectrum for each of the target locations 44 (except that the carbon-coated metal base plate 10 (or bipolar plate 100) is substituted for the reference plate 46). The integrated intensity of the Raman carbon signal derived from the observed Raman shift spectrum at each target location 44 may then be converted into a calculated thickness of the submicron carbon coating 42 by referencing the linear correlation previously developed. In particular, the integrated intensity of the Raman carbon signal for each of the one or more target locations 44 can simply be entered into the $y=mx$ equation to translate the integrated intensity of the Raman carbon signal into the calculated thickness; that is, the the integrated intensity of the Raman carbon signal for each of the one or more target locations 44 may be input as the "y" variable that has been developed using the reference plates 46 to arrive at the calculated thickness ("x" variable) of the submicron carbon coating 42 at the target location(s).

More than one carbon-coated metal plate 10 may have the thickness of their submicron carbon coatings 42 determined at the target location(s) 44 using the same relationship. For example, after the relationship between the Raman shift spectrum and the thickness of the submicron carbon coating 42 is established, multiple carbon-coated metal base plates 32 may be analyzed one after another. The relationship between the Raman shift spectrum and the thickness of the submicron carbon coating 42 (e.g., the linear correlation in the form of the equation $y=mx$) may be intermittently calibrated every so often depending on how the disclosed method is being implemented and in what setting (quality control, durability testing, failure analysis, etc.). Such calibration can be performed by going through the same process described above in connection with FIGS. 5-8 using the reference plates 46 in an effort to counteract any variances that may occur in the Raman spectrometer 48 or elsewhere in the overall process. Under certain circumstances, the linear correlation may be calibrated twice a day, daily, weekly, monthly, or after analyzing a certain number of carbon-coated metal plates 10 such as 10, 30, 50, or 100.

The disclosed method as described above can be programmed into conventional process automation software and carried out by conventional computer-controllable equipment and related accessories. In operation, for instance, the portable Raman spectrometer 50 can be successively carried to, and Raman spectroscopy performed at, each of the sample locations 44' on the reference plates 46 to acquire all of the intended Raman shift data for the reference plates 46. Associated computer equipment is able to sort and compile the Raman shift spectrums and to further calculate the linear correlation between the integrated intensity of the Raman carbon signals 78 (i.e., the integrated intensity data points 82) and the thicknesses of the submicron carbon coating 42' observed at the sample locations 44'. The same or different computer equipment can then associate the established linear correlation with the target locations 44 of the carbon-coated metal base plates 10 that are to be analyzed and can further reference the linear correlation in order to convert Raman shift spectrums obtained at each of the target locations 44 into the calculated thickness of the submicron carbon coating 42. The disclosed method can easily be practiced in laboratories or in manufacturing facilities.

The above description of preferred exemplary embodiments and specific examples are merely descriptive in nature; they are not intended to limit the scope of the claims that follow. Each of the terms used in the appended claims should be given its ordinary and customary meaning unless specifically and unambiguously stated otherwise in the specification.

What is claimed is:

1. A method of determining a thickness of a submicron carbon coating of a carbon-coated metal base plate, the method comprising:
  providing a carbon-coated metal base plate that includes a metal base plate and an exteriorly-exposed submicron carbon coating over the metal base plate;
  conducting Raman spectroscopy at a target location of the carbon-coated metal base plate to obtain a Raman shift spectrum for the target location; and
  converting the Raman shift spectrum obtained at the target location into a calculated thickness of the submicron carbon coating at the target location, wherein converting the Raman shift spectrum obtained at the target location into the calculated thickness of the submicron carbon coating at the target location comprises:
    isolating a Raman carbon signal from the Raman shift spectrum obtained at the target location for the carbon-coated metal base plate;
    integrating the Raman carbon signal isolated from the Raman shift spectrum over a defined wavenumber range to derive an integrated intensity of the Raman carbon signal;
    establishing a linear correlation over the defined wavenumber range between (1) an integrated intensity of a Raman carbon signal obtained from each of a series of reference plates that includes a submicron carbon coating having a verified thickness and (2) the verified thicknesses of the submicron carbon coatings of the series of reference plates; and
    referencing the linear correlation to convert the integrated intensity of the Raman carbon signal isolated from the Raman shift spectrum into the calculated thickness of the submicron carbon coating at the target location.

2. The method set forth in claim 1, wherein the carbon-coated metal base plate is a metallic bipolar plate that has a first major face that defines a first gas flow field and a second major face that defines a second gas flow field.

3. The method set forth in claim 2, wherein the metal base plate of the bipolar plate is composed of stainless steel.

4. The method set forth in claim 3, wherein a titanium interlayer is disposed between the metal base plate, which is composed of stainless steel, and the exteriorly-exposed submicron carbon coating.

5. The method set forth in claim 1, wherein establishing the linear correlation between the integrated intensity of the Raman carbon signals obtained from the series of reference plates and the verified thicknesses of the submicron carbon coatings of the series of reference plates comprises:
  conducting Raman spectroscopy at a sample location on each of the series of reference plates to obtain a Raman shift spectrum associated with the sample location on each of the reference plates, each of the series of reference plates having the same layered construction as the carbon-coated metal base plate and including a submicron carbon coating of a verified thickness in which the verified thickness of the submicron carbon coating on each of the series of reference plates is different;
  isolating a Raman carbon signal from the Raman shift spectrum obtained at the sample location of each of the reference plates;
  integrating the Raman carbon signal isolated from the Raman shift spectrum obtained at the sample location of each of the reference plates over the defined wavenumber range to derive an integrated intensity of the Raman carbon signal associated with each reference plate;
  deriving a linear equation in the form of y=mx that fits the integrated intensity of the Raman carbon signals associated with the reference plates when plotted against the verified thicknesses of the submicron carbon coatings of the reference plates, wherein "y" corresponds to the integrated intensity of the Raman carbon signal isolated from the Raman shift spectrum obtained at the sample locations over the defined wavenumber range, "x" corresponds to the verified thickness of the submicron carbon coating at the sample locations, and "m" is the slope representing the change in the integrated intensity of the Raman carbon signal over the change in the verified thickness of the submicron carbon coatings.

6. The method set forth in claim 1, wherein the defined wavenumber range is 900 $cm^{-1}$ to 1800 cm'.

7. The method set forth in claim 1, comprising:
  conducting Raman spectroscopy at a plurality of target locations spread across a surface of the carbon-coated metal base plate to obtain a Raman shift spectrum for each of the plurality of target locations; and
  converting the Raman shift spectrum obtained at each of the plurality of target locations into a calculated thickness of the submicron carbon coating at each of the plurality of target locations.

8. The method set forth in claim 7, further comprising:
  comparing the calculated thickness of the submicron carbon coating at each of the plurality of target locations against a minimum required coating thickness for the submicron carbon coating to verify whether the submicron carbon coating meets or exceeds the minimum required coating thickness across the surface of the carbon-coated metal base plate.

9. A method of determining a thickness of a submicron carbon coating of a carbon-coated metal base plate, the method comprising:
  directing a beam of monochromatic light at each of a plurality of target locations spread across a surface of a carbon-coated metal base plate;
  detecting inelastic scattered light reemitted from each of the plurality of target locations to obtain a Raman shift spectrum for each of the plurality of target locations;
  isolating a Raman carbon signal from the Raman shift spectrum obtained at each of the plurality of target locations;
  integrating the Raman carbon signal isolated from the Raman shift spectrum obtained at each of the plurality of target locations over a defined wavenumber range to derive an integrated intensity of the Raman carbon signal for each of the plurality of target locations;
  establishing a linear correlation over the defined wavenumber range between (1) an integrated intensity of a Raman carbon signal obtained from each of a series of reference plates that includes a submicron carbon coating having a verified thickness and (2) the verified thicknesses of the submicron carbon coatings of the series of reference plates; and
  referencing the linear correlation to convert the Raman carbon signal isolated from the Raman shift spectrum obtained at each of the plurality of target locations into a calculated thickness of the submicron carbon coating at each of the plurality of target locations.

10. The method set forth in claim 9, further comprising:
  comparing the calculated thickness of the submicron carbon coating at each of the plurality of target locations against a minimum required coating thickness of the submicron carbon coating to verify whether the submicron carbon coating meets or exceeds the minimum required coating thickness across the surface of the carbon-coated metal base plate.

11. The method set forth in claim 9, wherein the carbon-coated metal base plate is a metallic bipolar plate that has a first major face that defines a first gas flow field and a second major face that defines a second gas flow field.

12. The method set forth in claim 11, wherein the metal base plate of the bipolar plate is composed of stainless steel.

13. The method set forth in claim 12, wherein a titanium interlayer is disposed between the metal base plate, which is composed of stainless steel, and the submicron carbon coating.

14. The method set forth in claim 11, wherein the plurality of target locations includes anywhere from two to forty target locations.

15. The method set forth in claim 9, wherein the defined wavenumber range is 900 $cm^{-1}$ to 1800 $cm^{-1}$.

16. The method set forth in claim 9, wherein the linear correlation is a linear equation in the form of y=mx in which "y" corresponds to the integrated intensity of the Raman carbon signal isolated from the Raman shift spectrum obtained at the sample locations over the defined wavenumber range, "x" corresponds to the verified thickness of the submicron carbon coating at the sample locations, and "m" is the slope representing the change in the integrated intensity of the Raman carbon signal over the change in the verified thickness of the submicron carbon coatings.

17. A method of determining a thickness of a submicron carbon coating of a metallic bipolar plate, the method comprising:

providing a metallic bipolar plate that includes a metal base plate and an exteriorly-exposed submicron carbon coating overlying the metal base plate, the bipolar plate having a first major face that defines a first gas flow field and an oppositely-facing second major face that defines a second gas flow field;

determining a calculated thickness of the submicron carbon coating at a plurality of target locations spread across at least one of the first major face or the second major face of the bipolar plate, wherein determining the calculated thickness at each of the plurality of target locations comprises:

conducting Raman spectroscopy at the target location to obtain a Raman shift spectrum for the target location;

integrating a Raman carbon signal isolated from the Raman shift spectrum over a defined wavenumber range to derive an integrated intensity of the Raman carbon signal;

establishing a linear correlation over the defined wavenumber range between (1) an integrated intensity of a Raman carbon signal obtained from each of a series of reference plates that includes a submicron carbon coating having a verified thickness and (2) the verified thicknesses of the submicron carbon coatings of the series of reference plates; and referencing the linear correlation to determine the calculated thickness of the submicron carbon coating at the target location; and comparing the calculated thickness of the submicron carbon coating at each of the plurality of target locations against a minimum required coating thickness for the submicron carbon coating to verify whether the submicron carbon coating meets or exceeds the minimum required coating thickness across at least one of the first major face or the second major face of the bipolar plate.

18. The method set forth in claim 17, wherein the defined wavenumber range is 900 $cm^{-1}$ to 1800 $cm^{-1}$.

* * * * *